US 11,109,743 B2

(12) United States Patent
Nakamura

(10) Patent No.: US 11,109,743 B2
(45) Date of Patent: Sep. 7, 2021

(54) ENDOSCOPE APPARATUS

(71) Applicant: OLYMPUS CORPORATION, Tokyo (JP)

(72) Inventor: Sho Nakamura, Hachioji (JP)

(73) Assignee: OLYMPUS CORPORATION, Tokyo (JP)

(*) Notice: Subject to any disclaimer, the term of this patent is extended or adjusted under 35 U.S.C. 154(b) by 354 days.

(21) Appl. No.: 16/241,212

(22) Filed: Jan. 7, 2019

(65) Prior Publication Data

US 2019/0133422 A1 May 9, 2019

Related U.S. Application Data

(63) Continuation of application No. PCT/JP2016/070438, filed on Jul. 11, 2016.

(51) Int. Cl.
*A61B 1/00* (2006.01)
*A61B 1/12* (2006.01)
(Continued)

(52) U.S. Cl.
CPC ...... *A61B 1/00188* (2013.01); *A61B 1/00006* (2013.01); *A61B 1/00096* (2013.01);
(Continued)

(58) Field of Classification Search
CPC . A61B 1/00188; A61B 1/128; A61B 1/00006; A61B 1/00096; A61B 1/05;
(Continued)

(56) References Cited

U.S. PATENT DOCUMENTS

| 8,084,969 B2* | 12/2011 | David | G01D 5/145 |
| | | | 318/135 |
| 2005/0036775 A1* | 2/2005 | Morimoto | H04N 5/2254 |
| | | | 396/67 |
| 2010/0254032 A1* | 10/2010 | Matsuki | G02B 7/102 |
| | | | 359/824 |
| 2012/0162402 A1* | 6/2012 | Amano | A61B 1/00188 |
| | | | 348/65 |

(Continued)

FOREIGN PATENT DOCUMENTS

| CN | 103006169 A | 4/2013 |
| JP | 2006000660 A * | 1/2006 |

(Continued)

OTHER PUBLICATIONS

International Search Report dated Sep. 20, 2016 issued in PCT/JP2016/070438.

*Primary Examiner* — Timothy J Neal
*Assistant Examiner* — Sung Ham
(74) *Attorney, Agent, or Firm* — Scully, Scott, Murphy & Presser, P.C.

(57) ABSTRACT

An endoscope apparatus includes an endoscope including an observation optical system including a lens drive mechanism and a video processor connected to the endoscope, and the endoscope apparatus includes a voice coil motor provided in the endoscope and configured to drive a lens relating to the lens drive mechanism and a position detecting apparatus provided in the endoscope and configured to detect a position of the lens. The video processor is configured to determine whether or not the position detecting apparatus is in a heat generating state, and halt actuation of the position detecting apparatus if the video processor determines that the position detecting apparatus is in the heat generating state.

14 Claims, 5 Drawing Sheets

(51) Int. Cl.
*A61B 1/05* (2006.01)
*A61B 1/06* (2006.01)
*G02B 23/24* (2006.01)
*A61B 1/07* (2006.01)

(52) U.S. Cl.
CPC .............. *A61B 1/05* (2013.01); *A61B 1/0676* (2013.01); *A61B 1/128* (2013.01); *G02B 23/2476* (2013.01); *A61B 1/00147* (2013.01); *A61B 1/07* (2013.01); *G02B 23/2438* (2013.01)

(58) Field of Classification Search
CPC ..... A61B 1/0676; A61B 1/00147; A61B 1/07; G02B 23/2476; G02B 23/2438
See application file for complete search history.

(56) References Cited

U.S. PATENT DOCUMENTS

| | | | |
|---|---|---|---|
| 2013/0030248 A1* | 1/2013 | Matsumaru | A61B 1/00027 600/110 |
| 2013/0035545 A1* | 2/2013 | Ono | A61B 1/045 600/109 |
| 2013/0308933 A1* | 11/2013 | Uchiyama | H04N 5/23212 396/125 |
| 2016/0037079 A1 | 2/2016 | Gocho et al. | |
| 2017/0031128 A1* | 2/2017 | Liu | G02B 7/04 |

FOREIGN PATENT DOCUMENTS

| | | | |
|---|---|---|---|
| JP | 4339823 B2 | | 10/2009 |
| JP | 2012-253991 A | | 12/2012 |
| WO | WO 2015/015877 A1 | | 2/2015 |
| WO | WO 2015015877 | * | 2/2015 |

* cited by examiner

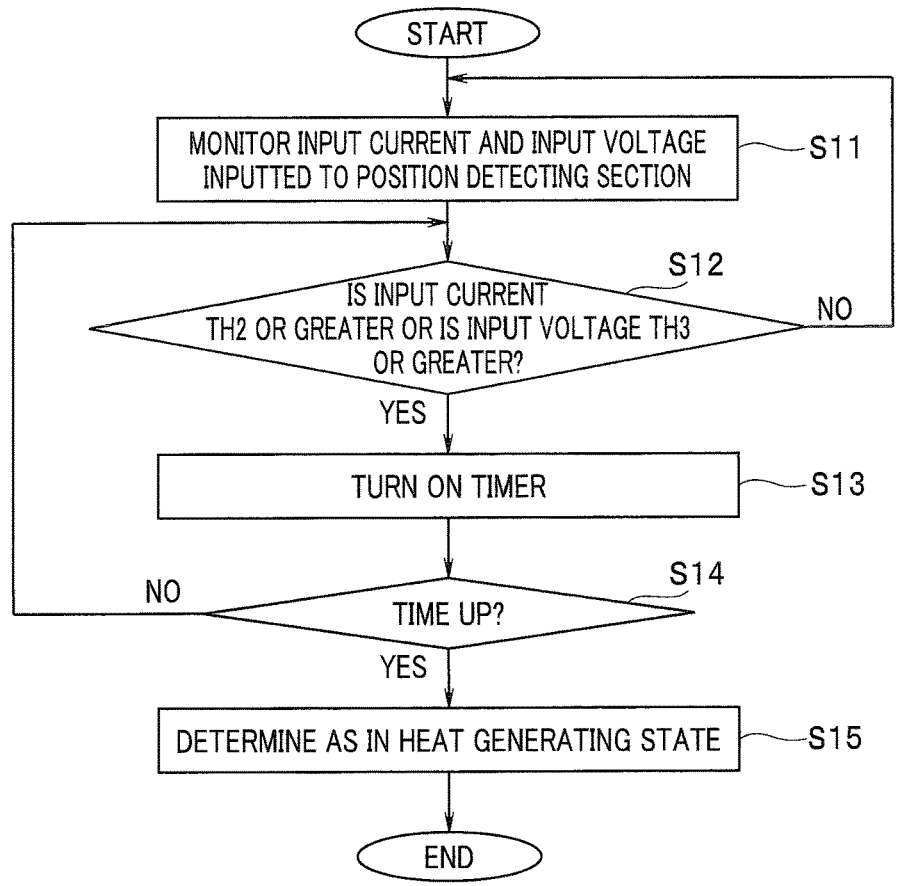
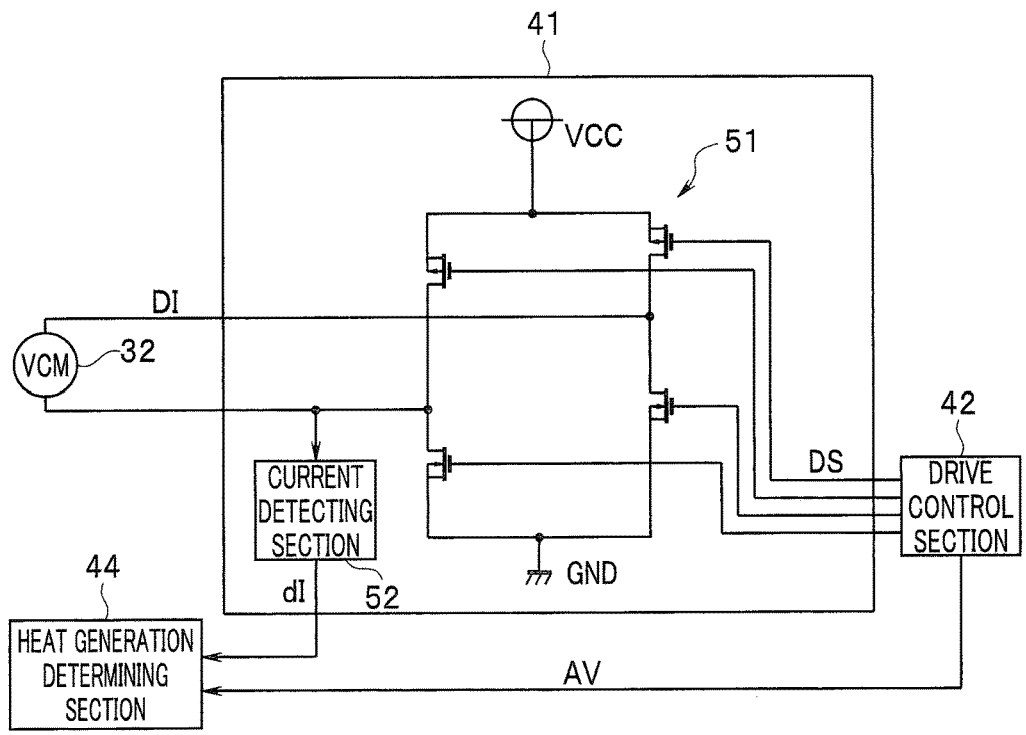

ENDOSCOPE APPARATUS

CROSS REFERENCE TO RELATED APPLICATION

This application is a continuation application of PCT/JP2016/070438 filed on Jul. 11, 2016, the entire contents of which are incorporated herein by this reference.

BACKGROUND OF THE INVENTION

Field of the Invention

The present invention relates to an endoscope apparatus including an actuator in a distal end portion of an insertion portion.

Description of the Related Art

Endoscopes have been used in a medical field and an industrial field. Also, endoscopes each having a zoom function that causes an actuator to move a lens to change a magnification of an observation image have been proposed.

Also, for example, Japanese Patent No. 4339823 proposes an endoscope apparatus including an endoscope including a zoom lens driven by an actuator, in which in order to prevent deterioration in characteristics of the actuator or decrease in life of the actuator due to generation of heat by the actuator, a current flowing in the actuator is detected to determine whether or not the actuator is in a shorted state, an open state or a heat generating state.

In order to more precisely drive an actuator used in an endoscope apparatus by means of feedback control, a position detecting section configured to detect a position of a zoom lens is provided in a distal end portion of an insertion portion of the endoscope.

SUMMARY OF THE INVENTION

An endoscope apparatus according to an aspect of the present invention is an endoscope apparatus including: an endoscope including an observation optical system including a lens drive mechanism; and an image processing apparatus including a processor including hardware, the image processing apparatus being connected to the endoscope, the endoscope apparatus including: an actuator provided in the endoscope and configured to drive a lens relating to the lens drive mechanism; and a position detecting apparatus provided in the endoscope and configured to detect a position of the lens, the processor being configured to determine whether or not the position detecting apparatus is in a heat generating state, and halt actuation of the position detecting apparatus, if the processor determines that the position detecting apparatus is in the heat generating state.

BRIEF DESCRIPTION OF THE DRAWINGS

FIG. 6 is a flowchart illustrating an example of a heat generation determining section 45 for a position detecting section, according to the embodiment of the present invention; and FIG. 7 is a circuit diagram of a voice coil motor driver 41 where whether or not an actuator is in a heat generating state is determined based on a resistance value of the actuator, according to modification 1 of the embodiment of the present invention.

DETAILED DESCRIPTION OF THE PREFERRED EMBODIMENT

An embodiment of the present invention will be described below with reference to the drawings.

(Overall Configuration)

Figure 1:
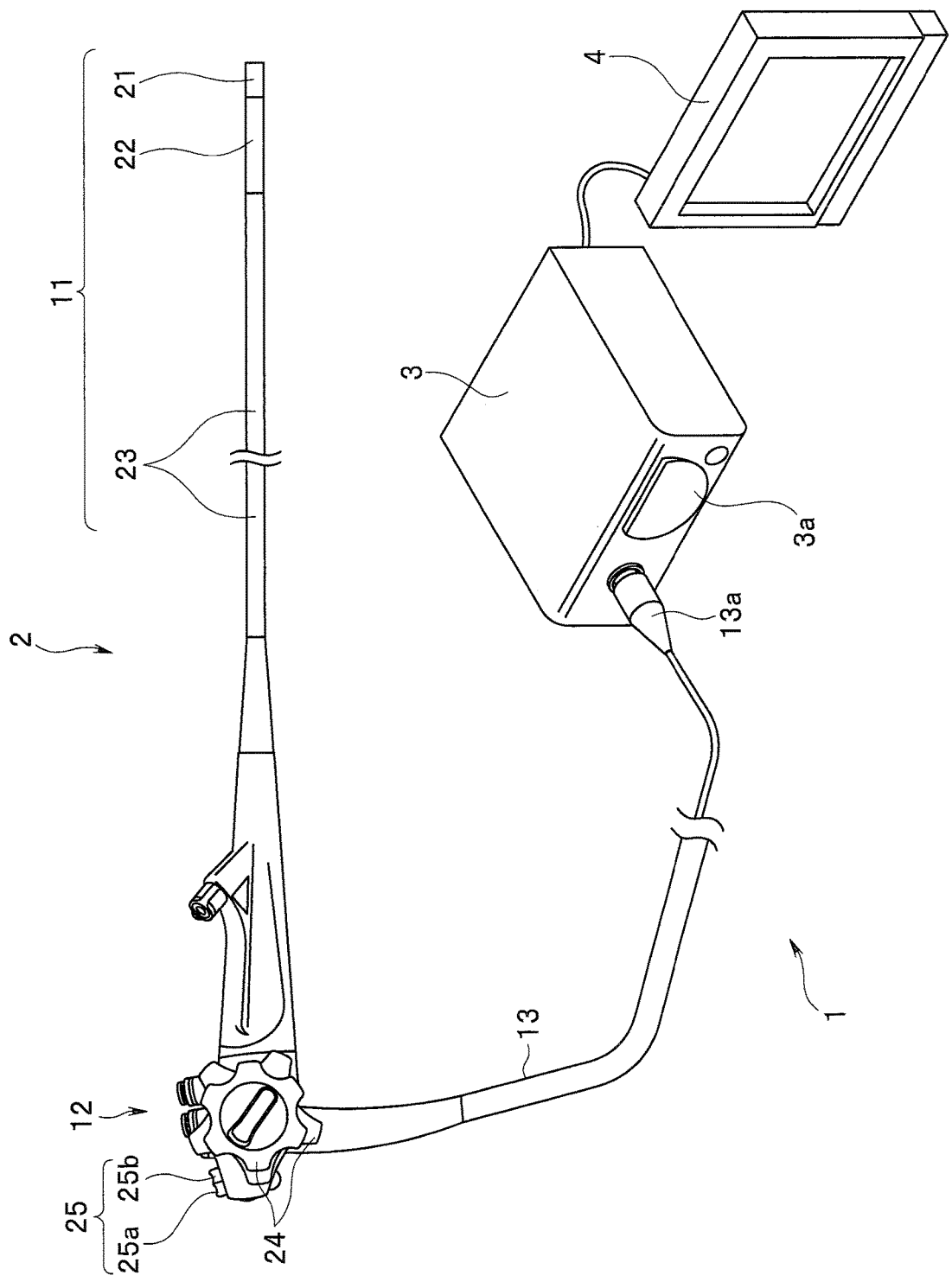
FIG. 1 is a configuration diagram illustrating a configuration of an endoscope apparatus according to an embodiment of the present invention.

FIG. 1 is a configuration diagram illustrating a configuration of an endoscope apparatus according to the present embodiment. As illustrated in FIG. 1, an endoscope apparatus 1 according to the present embodiment includes an endoscope 2 and a video processor 3 connected to the endoscope 2. A monitor 4 is connected to the video processor 3.

The endoscope 2 is an electronic endoscope including an elongated insertion portion 11, an operation portion 12 connected to a proximal end of the insertion portion 11 and a universal cable 13 extending from the operation portion 12.

The insertion portion 11 of the endoscope 2 includes a rigid distal end portion 21 at a distal end, a bendable bending portion 22 is provided adjacent to the distal end portion 21, and a long flexible tube portion 23 is further provided on the proximal end side of the bending portion 22.

Figure 2:
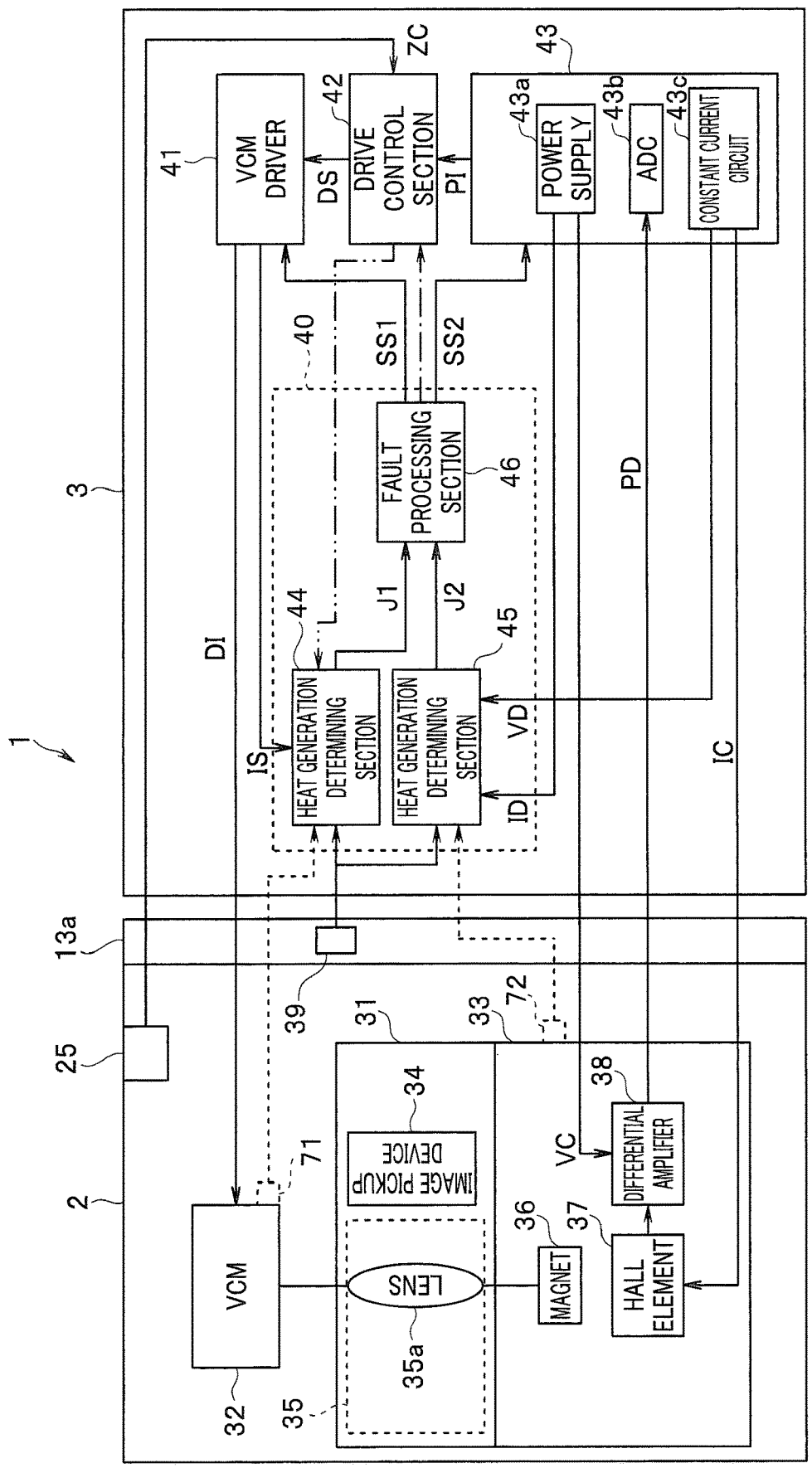
FIG. 2 is a block diagram illustrating a configuration of an endoscope apparatus 1 according to the embodiment of the present invention.

The distal end portion 21 incorporates an image pickup device 34 and an image pickup optical system 35 (FIG. 2). In the distal end portion 21, an observation window (not illustrated) is provided, and light from an object falls on a light receiving surface of the image pickup device 34 through the observation window and the image pickup optical system 35. The image pickup optical system 35 is an observation optical system including a zoom mechanism. An image pickup signal obtained in the image pickup device 34 is supplied to the video processor 3 via a signal wire inserted inside the insertion portion 11, the operation portion 12 and the universal cable 13.

Note that the image pickup optical system 35 is an observation optical system including a zoom mechanism that enables change of an image pickup magnification ratio, but may be an observation optical system including a mechanism configured to drive a lens, which is not a zoom mechanism. In other words, the image pickup optical system 35 only needs to include a lens drive mechanism.

Note that various signals wires for transmission of, e.g., a drive signal and a detection signal between an actuator and a position detecting section, which will be described later, are inserted inside the universal cable 13.

Furthermore, an illumination window (not illustrated) is also provided in the distal end portion 21. Illuminating light is outputted from the illumination window.

A user of the endoscope apparatus 1 can cause the bending portion 22 to bend by operating a bending knob 24 provided at the operation portion 12.

At the operation portion 12, various types of operation devices such as a release button, and a later-described zoom operation device 25 for driving a zoom lens are provided.

The zoom operation device 25 includes a button 25a for zooming to the tele side of the zoom mechanism and a button 25b for zooming to the wide side of the zoom mechanism. When the user presses the button 25a, while the button 25a is pressed, a zoom lens 35a (FIG. 2) moves so as to zoom to the tele side, and when the user stops pressing the button 25a, the zoom lens 35a halts at a zoom position at that point of time. Likewise, when the user presses the button 25b, while the button 25b is pressed, the zoom lens 35a moves to zoom to the wide side, and when the user stops pressing the button 25b, the zoom lens 35a halts at a zoom position at that point of time. Therefore, the user can observe an object at a desired zoom position or with a desired zoom amount by pressing the buttons 25a and 25b.

Note that the zoom operation device 25 is formed of the two buttons 25a, 25b provided at the operation portion 12 of the endoscope 2, but may be another operation device such as a foot switch connected to the video processor 3.

A connector 13a is provided at a distal end of the universal cable 13 extending from the operation portion 12. The connector 13a can be detachably attached to the video processor 3.

The video processor 3 includes a light source apparatus including a light source, such as a lamp, configured to generate illuminating light, and the illuminating light is inputted to a proximal end face of an optical fiber (not illustrated) inserted inside the insertion portion 11, the operation portion 12 and the universal cable 13 and is outputted from the illumination window at the distal end of the insertion portion 11.

Note that the illuminating light may be light from a light-emitting element, such as an LED (light-emitting diode), incorporated inside the distal end portion 21.

The video processor 3 is an image processing apparatus which incorporates a control section 40 (FIG. 2) for controlling the entire endoscope apparatus 1. The control section 40 includes, e.g., a central processing unit (CPU), a ROM, a RAM and various types of interfaces, and the user can perform various operations using, e.g., various buttons at the operation portion 12 and an operation panel 3a of the video processor 3. The video processor 3 executes a program according to various functions in response to an operation performed by the user.

The video processor 3 is a processor configured to receive an input of an image pickup signal from the endoscope 2 and generate an endoscopic image, which is an image of a subject. An image signal of an endoscopic image is outputted to the monitor 4 and the endoscopic image is displayed on the monitor 4.

The endoscope 2 has a zoom function, and the user can cause an endoscopic image with a view angle desired by the user to be displayed on the monitor 4, by operating the zoom operation device 25. The video processor 3 drives the actuator in the endoscope 2 in response to an operation of the zoom operation device 25 by the user.

As described above, the endoscope apparatus 1 includes the endoscope 2 including an observation optical system including a lens drive mechanism and the video processor 3, which is a processor to which the endoscope 2 is connected.

FIG. 2 is a block diagram illustrating a configuration of the endoscope apparatus 1.

The endoscope 2 includes an image pickup section 31, a voice coil motor 32, which serves as an actuator, and a position detecting section 33. The image pickup section 31, the voice coil motor (VCM) 32 and the position detecting section 33 are provided inside the distal end portion 21 of the insertion portion 11.

The image pickup section 31 includes the image pickup device 34 such as a CCD image sensor, and the image pickup optical system 35. The image pickup optical system 35 is a zoom optical system and includes the zoom lens 35a, which is a movable lens. The image pickup device 34 receives light of an object image through the image pickup optical system 35, via a light receiving surface and performs photoelectric conversion of the light and outputs an image pickup signal.

The voice coil motor 32 is an actuator provided in the endoscope 2 and configured to drive a lens relating to a lens drive mechanism. Here, the voice coil motor 32 moves the zoom lens 35a in an optical axis direction of the image pickup optical system 35. The voice coil motor 32 is an electric actuator that includes a coil and a magnet and is driven by a drive current DI.

The zoom lens 35a is connected to a movable portion of the voice coil motor 32, and can be moved in the optical axis direction of the image pickup optical system 35 by the voice coil motor 32, by moving the movable portion relative to a fixed portion inside the voice coil motor 32.

As described above, the actuator provided in the distal end portion 21 is a voice coil motor including one or more magnets and one or more coils and enabling moving the movable portion relative to the fixed portion.

When the user presses the above-described button 25a or 25b, a zoom instruction signal ZC is outputted from the zoom operation device 25. Based on the zoom instruction signal ZC, a later-described drive control section 42 outputs a drive instruction signal DS for driving the voice coil motor 32, to move the zoom lens 35a. The movement of the zoom lens 35a changes the zoom position in the image pickup optical system 35, resulting in change in scale of the object image displayed on the monitor 4.

The position detecting section 33 as a position detecting apparatus is a sensor apparatus provided in the endoscope 2 and configured to detect a position of a lens relating to a zoom mechanism. More specifically, the position detecting section 33 includes a magnet 36, a Hall element 37 and a differential amplifier 38. The magnet 36 is connected and fixed to the zoom lens 35a and the magnet 36 moves together with the zoom lens 35a.

The Hall element 37 is a sensor configured to upon being driven by an input current IC, which is a drive current from a later-described constant current circuit 43c, detect a magnetic field of the magnet 36. The Hall element 37 outputs an analog signal according to a magnitude of the detected magnetic field. Note that for the position detection sensor, a magnetic resistance element may be employed instead of a Hall element.

As described above, the position detecting section 33 includes a Hall element or a magnetic resistance element configured to detect a change of a magnetic field resulting from movement of the zoom lens 35a, and the Hall element or the magnetic resistance element receives supply of a constant current from the constant current circuit 43c.

The differential amplifier 38 amplifies an analog signal from the Hall element 37 and outputs a voltage signal according to the analog signal as a position detection signal PD. In other words, the position detecting section 33 detects a position of the zoom lens 35a driven by the voice coil motor 32 and outputs a position detection signal PD.

Note that the voice coil motor 32 is used as an actuator and the Hall element 37 configured to detect a magnetic field of the magnet 36 as a position detection sensor, but the actuator may be a device other than a voice coil motor, the position detection sensor may be a sensor other than a Hall element and the detection may be detection of a physical amount other than detection of a magnetic field.

The connector 13a of the universal cable 13 of the endoscope 2 incorporates a non-volatile memory 39. In the memory 39, various pieces of threshold information for later-described heat generation determination are stored. In order to respond to a case where characteristics and configurations of the actuator (here, the voice coil motor) and the position detecting section 33 differ depending on endoscopes, various pieces of threshold information are held in the endoscope 2.

As described above, the endoscope 2 includes the memory 39 that stores determination information for later-described heat generation determining sections 44, 45 to determine that the actuator and the position detecting section are in a heat generating state, respectively.

Note that if common threshold information can be used for a plurality of endoscopes that can be connected to the video processor 3, various pieces of threshold information may be stored in a storage apparatus such as a ROM in the video processor 3.

When the endoscope 2 is connected to the video processor 3, various pieces of threshold information recorded in the memory 39 are read by the video processor 3.

The video processor 3 includes a control section 40, a voice coil motor (VCM) driver 41, a drive control section 42 and a position detecting circuit 43.

The control section 40 performs control of driving of the voice coil motor 32 in addition to overall operation of the endoscope apparatus 1, various types of image generation and various types of processing according to various functions. The control section 40 is a processor which includes hardware such as a central processing unit (CPU), a ROM and a RAM, which are not illustrated, and processing for later-described heat generation determination, etc., is performed by execution of a program stored in the ROM. FIG. 2 only illustrates a plurality of blocks relating to control of driving of the voice coil motor 32.

The control section 40 includes the heat generation determining section 44 for the actuator, the heat generation determining section 45 for the position detecting section, and a fault processing section 46. The heat generation determining section 44 is a processing section configured to determine that the voice coil motor 32, which is an actuator, is in a heat generating state. The heat generation determining section 45 is a processing section configured to determine that the position detecting section 33 is in a heat generating state.

Note that, in the embodiment of the present invention, the control section 40 is a processor which includes a CPU and which executes the processing of the heat generation determining sections 44, 45 and the processing of the fault processing section 46 by software. However, the control section 40 as the processor may include a circuit such as a logic circuit or an analog circuit which performs is some of or all of the processings, and may also include at least one of ASIC (Application Specific Integrated Circuit) and FPGA (Field-Programmable Gate Array), for example.

The voice coil motor driver 41 is a circuit configured to generate a drive current DI for the voice coil motor 32 and output the drive current DI to the voice coil motor 32 and supply a current signal IS indicating a current value of the current supplied to the voice coil motor 32 to the heat generation determining section 44.

The drive control section 42 is a circuit configured to generate a drive instruction signal DS according to a zoom instruction signal ZC from the zoom operation device 25 and zoom position information PI from the position detecting circuit 43 and output the drive instruction signal DS to the voice coil motor driver 41. More specifically, the drive control section 42 performs feedback control of a zoom position based on the zoom position information PI from the position detecting circuit 43, and generates a drive instruction signal DS as a control signal and outputs the drive instruction signal DS to the voice coil motor driver 41 so that the zoom lens 35a reaches a zoom position designated by the zoom instruction signal ZC.

The position detecting circuit 43 includes a power supply 43a, an analog-digital converter (hereinafter abbreviated as "ADC") 43b and the constant current circuit 43c.

The power supply 43a is a circuit configured to supply an input voltage VC, which is a power supply voltage, to the differential amplifier 38 via a signal wire and supply a current signal ID indicating a current value of a current flowing in the signal wire through which the input voltage VC is supplied, to the heat generation determining section 45 for the position detecting section.

The ADC 43b converts a position detection signal PD, which is an analog output of the differential amplifier 38, into zoom position information PI, which is a digital signal.

The constant current circuit 43c is a circuit configured to supply an input current IC to the Hall element 37 via a signal wire and supply a voltage signal VD indicating a voltage value of a voltage applied to the Hall element 37 to the heat generation determining section 45 for the position detecting section.

As described above, the user can designate a desired zoom position by pressing the button 25a or 25b. When the user stops pressing the button 25a or 25b, a zoom position, that is, a zoom amount is determined. The drive control section 42 generates a drive instruction signal DS so that a zoom amount corresponding to a position detection signal PD detected by the position detecting section 33 matches a zoom position that is a target value designated by the user, and outputs the drive instruction signal DS to the voice coil motor driver 41. The voice coil motor driver 41 outputs a drive current DI according to the drive instruction signal DS to the voice coil motor 32.

The heat generation determining section 44 for the actuator monitors the current value of the drive current DI outputted by the voice coil motor driver 41, via the current signal IS and determines whether or not the voice coil motor 32 is in a heat generating state, using threshold information, which is determination information read from the memory 39.

The heat generation determining section 45 for the position detecting section monitors the input current IC supplied to the Hall element 37, via the voltage signal VD outputted by a voltage detecting circuit 63 (FIG. 4) and monitors the input voltage VC supplied to the differential amplifier 38, via the current signal ID outputted by the current detecting circuit 61 (FIG. 4), and determines whether or not the position detecting section 33 is in a heat generating state, using threshold information, which is determination information read from the memory 39.

A determination result information piece J1 from the heat generation determining section 44 and a determination result information piece J2 from the heat generation determining section 45 are supplied to the fault processing section 46.

The fault processing section 46 generates halt signals SS1, SS2 for necessary halt processing based on the two determination result information pieces J1, J2 and outputs the halt signals SS1, SS2 to the voice coil motor driver 41 and the position detecting circuit 43, respectively.

Figure 3:
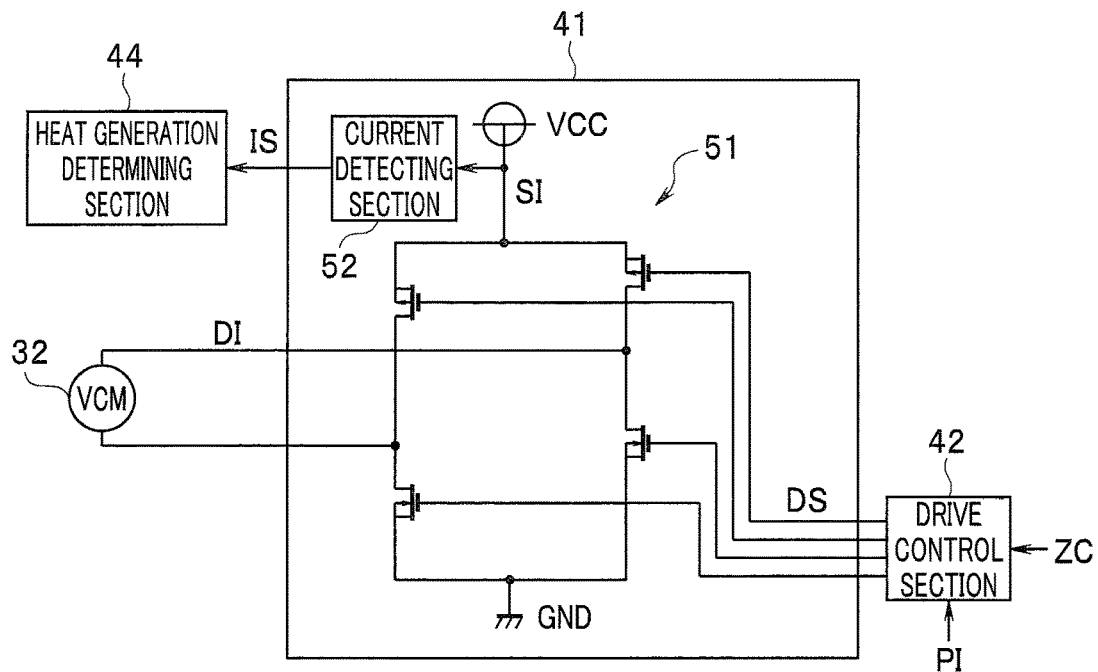
FIG. 3 is a circuit diagram illustrating a configuration of a voice coil motor driver 41 according to the embodiment of the present invention.

FIG. 3 is a circuit diagram illustrating a configuration of the voice coil motor driver 41.

The voice coil motor driver 41 includes an H-bridge circuit 51 and a current detecting section 52. The H-bridge circuit 51 is configured by parallel connection of two series circuits each including a P channel-type MOSFET and an N channel-type MOSFET connected in series, and a power supply voltage VCC is applied to the H-bridge circuit 51. The voice coil motor 32 is electrically connected between a point of connection between a P channel-type MOSFET and an N channel-type MOSFET on the one side and a point of connection between a P channel-type MOSFET and an N channel-type MOSFET on the other side. The drive instruction signal DS from the drive control section 42 is supplied to a gate of each MOSFET.

Where the voice coil motor 32 is driven by means of PWM control, the drive instruction signal DS is a signal for turning on/off the power supply voltage VCC at a designated duty ratio, and where the voice coil motor 32 is driven by means of linear control, the drive instruction signal DS is a signal for bringing the power supply voltage VCC into a designated voltage.

The current detecting section 52 is provided between the power supply voltage VCC and the H-bridge circuit 51 and detects a current SI flowing from the power supply voltage VCC to the H-bridge circuit 51. The current detecting section 52 outputs a current signal IS indicating a current value of the current SI and the current signal IS is supplied to the heat generation determining section 44.

Here, since the drive current DI supplied to the voice coil motor 32 may cause a short with a metal outer covering member inside the narrow distal end portion 21, resulting in change of a current path of the drive current DI along the way, the current detecting section 52 is provided not on a path of the drive current DI flowing in the voice coil motor 32 but between the power supply voltage VCC and the H-bridge circuit 51 of the voice coil motor driver 41.

Figure 4:
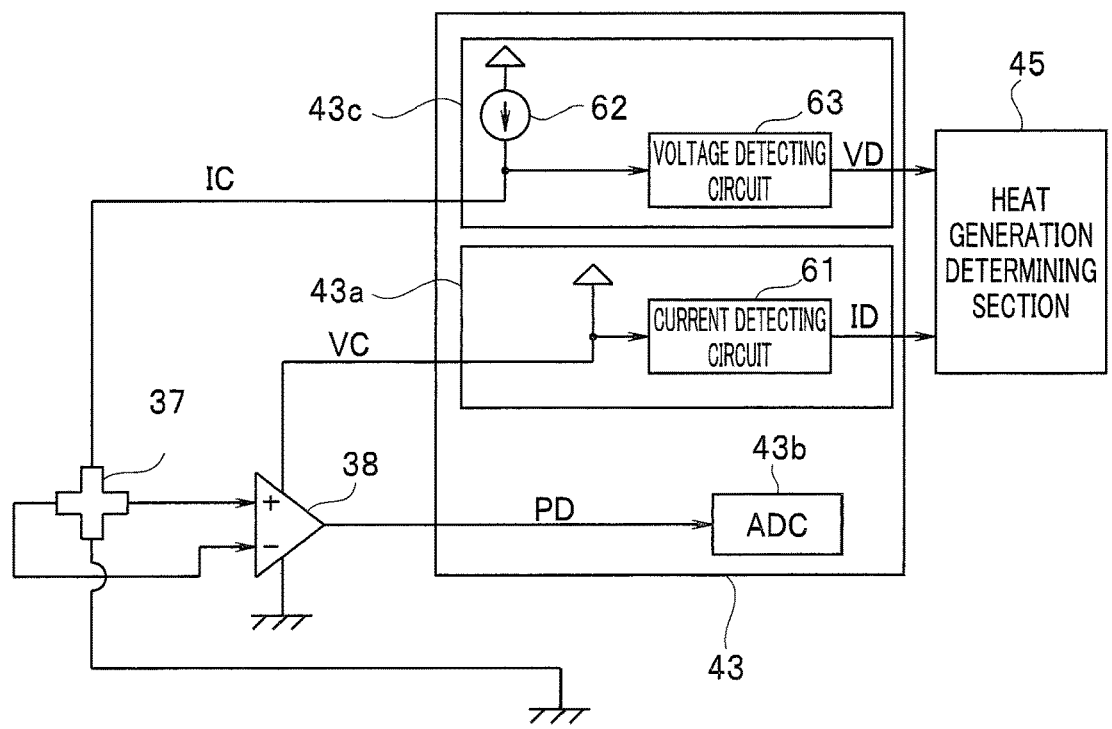
FIG. 4 is a circuit diagram illustrating a configuration of a position detecting circuit 43 according to the embodiment of the present invention.

FIG. 4 is a circuit diagram illustrating a configuration of the position detecting circuit 43.

The power supply 43*a* of the position detecting circuit 43 supplies an input voltage VC to the differential amplifier 38 and includes a current detecting circuit 61. The constant current circuit 43*c* of the position detecting circuit 43 includes a constant current source 62 and a voltage detecting circuit 63.

The current detecting circuit 61 detects a current signal flowing in the signal wire via which the power supply voltage VC for the differential amplifier 38 is supplied. The current detecting circuit 61 outputs a current signal ID indicating a current value of the current signal flowing in the signal wire, to the heat generation determining section 45.

The voltage detecting circuit 63 is connected to the signal wire in which an input current IC for the Hall element 37 flows, and detects a voltage applied to the Hall element 37. The voltage detecting circuit 63 outputs a voltage signal VD indicating a voltage value of the detected voltage, to the heat generation determining section 45.

(Operation)
(Heat Generation Determination)

Figure 5:
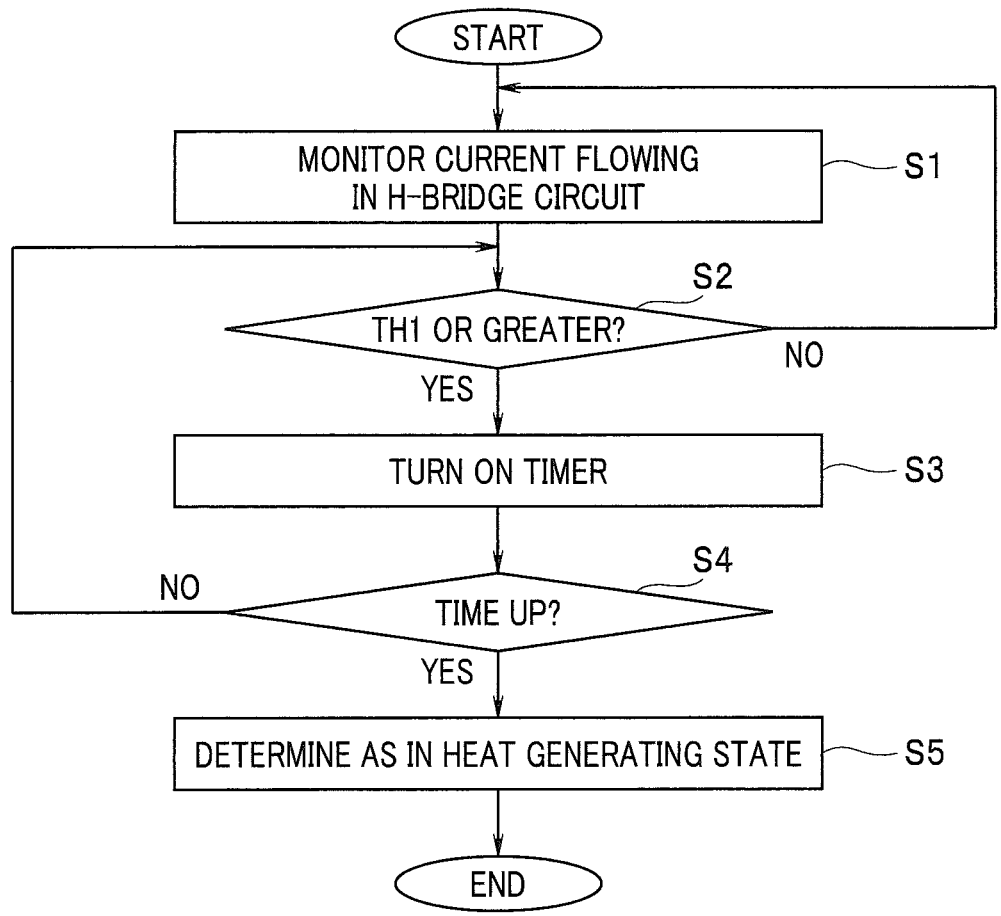
FIG. 5 is a flowchart illustrating an example of a flow of determination processing in a heat generation determining section 44 for an actuator, according to the embodiment of the present invention.

FIG. 5 is a flowchart illustrating an example of a flow of determination processing in the heat generation determining section 44 for the actuator. The determination processing in the heat generation determining section 44 illustrated in FIG. 5 is performed by the CPU of the control section 40.

The heat generation determining section 44 for the actuator monitors a current SI flowing in the H-bridge circuit 51 (step (hereinafter abbreviated as "S") 1). More specifically, the heat generation determining section 44 monitors a current value of a current signal IS that the current detecting section 52 outputs.

The heat generation determining section 44 determines whether or not a current value of the current SI flowing in the H-bridge circuit 51 is a predetermined threshold TH1 or greater (S2). The threshold TH1 is a piece of determination information read from the memory 39, and each of various predetermined thresholds and various predetermined time periods described below is also a piece of determination information read from the memory 39.

If the current value of the current SI is the predetermined threshold TH1 or greater (S2: YES), the heat generation determining section 44 turns on a timer configured to measure a predetermined time period T1 (S3). The timer is, for example, a software timer. Note that in S3, if the timer is already on, the timer is not turned on again. The predetermined time period T1 is, for example, a period of time ranging from several hundreds of milliseconds to several seconds.

If the current value of the current SI is not the predetermined threshold TH1 or greater (S2: NO), the processing returns to S1. Note that in the case of NO in S2, if the timer is already on, the timer is cleared.

After the timer is turned on, the heat generation determining section 44 determines whether or not the timer indicates that the time is up (S4).

If the time is not up (S4: NO), the processing returns to S2. Therefore, the result of the determination in S4 is "NO" until a state in which the current value of the current SI is the predetermined threshold TH1 or greater continues for the predetermined time period T1.

If the time is up (S4: YES), the heat generation determining section 44 determines that the voice coil motor 32, which is an actuator, is in a heat generating state (S5). In other words, since the current SI of a predetermined value or greater flows in the H-bridge circuit 51, the voice coil motor 32 is presumed or determined as generating heat. In S5, the timer is cleared.

Here, whether or not the current value of the current SI continues for the predetermined time period T1 or more is determined using the timer is to prevent erroneous heat generation determination based on an instantaneous current SI increase caused by noise due to electromagnetic waves from a medical device such as an electric surgical knife.

As described above, the heat generation determining section 44 monitors a supply current supplied to the voice coil motor 32 and if a value of the supply current is the threshold TH1 or greater and a state in which the value of the supply current is the threshold TH1 or greater continues for the predetermined time period T1, determines that the voice coil motor 32 is in a heat generating state.

FIG. 6 is a flowchart illustrating an example of a flow of determination processing in the heat generation determining section 45 for the position detecting section. The determination processing in the heat generation determining section 45 illustrated in FIG. 6 is also performed by the CPU of the control section 40.

The heat generation determining section 45 for the position detecting section monitors an input current IC and an input voltage VC inputted to the position detecting section 33 (S11). More specifically, the heat generation determining section 45 monitors a voltage signal VD outputted from the voltage detecting circuit 63 and a current signal ID outputted from the current detecting circuit 61.

The heat generation determining section 45 determines whether or not the input current IC is a predetermined threshold TH2 or greater or the input voltage VC is a predetermined threshold TH3 or greater (S12). More specifically, the heat generation determining section 45 determines whether or not the voltage signal VD that the voltage detecting circuit 63 outputs has a value of a predetermined threshold TH2 or greater or the current signal ID that the current detecting circuit 61 outputs has a value of a predetermined threshold TH3 or greater.

If the input current IC is the predetermined threshold TH2 or greater or the input voltage VC is the predetermined threshold TH3 or greater (S12: YES), the heat generation determining section 45 turns on a timer configured to measure a predetermined time period T2 (S13). The timer is, for example, a software timer. Note that in S13, if the timer is already on, the timer is not turned on again. The predetermined time period T2 is a period of time ranging from several hundreds of milliseconds to several seconds.

If the current value of the input current IC or the voltage value of the input voltage VC is not the predetermined threshold TH2 or greater or TH3 or greater, respectively (S12: NO), the processing returns to S11. Note that in the case of NO in S12, if the timer is already on, the timer is cleared.

After the timer is turned on, the heat generation determining section 45 determines whether or not the timer indicates that the time is up (S14).

If the time is not up (S14: NO), the processing returns to S12. Therefore, the result of the determination in S14 is "NO" until a state in which the current that is being monitored is the predetermined threshold TH2 or greater or the voltage that is being monitored is the predetermined threshold TH3 or greater continues for the predetermined time period T2.

If the time is up (S14: YES), the heat generation determining section 45 determines that the position detecting section 33 is in a heat generating state (S15). In other words, the heat generation determining section 45 monitors the input current IC or the input voltage VC inputted to the position detecting section 33, and if the value of the input current IC or the input voltage VC is the threshold TH2 or TH3 or greater, respectively, and a state in which the value of the input current IC or the input voltage VC is the threshold TH2 or TH3 or greater, respectively, continues for the predetermined time period T2, presumes or determines that the position detecting section 33 is in a heat generating state. In S15, the timer is cleared.

Here, whether or not a state in which the current value of the input current IC or the voltage value of the input voltage VC continues for the predetermined time period T2 or more is determined using the timer is to prevent the heat generation determining section 45 from making erroneous determination on whether or not the position detecting section 33 generates heat because of noise due to electromagnetic waves from a medical device such as an electric surgical knife.

Therefore, if a state in which the input current IC is the predetermined threshold TH2 or greater or the input voltage VC is the predetermined threshold TH3 or greater continues for the predetermined time period T2 or more, the heat generation determining section 45 determines that the position detecting section 33 is in a heat generating state.

(Fault Processing)

As a result of the processing in FIG. 5, if the heat generation determining section 44 determines that the voice coil motor 32 is in a heat generating state, the heat generation determining section 44 outputs a determination result information piece J1 to the fault processing section 46. As a result of the processing in FIG. 6, if the heat generation determining section 45 determines that the position detecting section 33 is in a heat generating state, the heat generation determining section 45 outputs a determination result information piece J2 to the fault processing section 46.

The fault processing section 46 is an actuation halting section configured to halt actuation of the voice coil motor 32 and actuation of the position detecting section 33 based on results of determination in the heat generation determining sections 44 and 45.

(1) Case where Only the Voice Coil Motor Generates Heat

If it is determined that the voice coil motor 32 is in a heat generating state and the position detecting circuit 43 is not in a heat generating state based on the determination result information pieces J1 and J2, the fault processing section 46 outputs a signal SS1 for halting actuation of the voice coil motor driver 41 to the voice coil motor driver 41. Note that as indicated by the alternate long and short dash line in FIG. 2, the halt signal SS1 may be outputted to the drive control section 42.

The actuation of the voice coil motor driver 41 is halted by making the drive current DI for the voice coil motor 32 be zero so as to prevent the voice coil motor 32 from generating heat or making the drive current DI for the voice coil motor 32 be equal to or below a predetermined current value that makes heat generated by the voice coil motor 32 be extremely small.

As a result, the drive current DI is no longer outputted to the voice coil motor 32.

Note that in this case, the fault processing section 46 outputs a halt signal S S1 for halting actuation of the voice coil motor driver 41 and a halt signal SS2 for halting actuation of the position detecting section 33 to the position detecting circuit 43. This is because, when actuation of the voice coil motor 32 is halted, the distal end portion 21 of the insertion portion 11 is more prevented from generating heat since actuation of the position detecting section 33 is no longer necessary either.

The actuation of the position detecting section 33 is halted by making the input current IC and the power supply voltage VC supplied to the position detecting section 33 be zero, respectively, so as to prevent the position detecting section 33 from generating heat or making the input current IC and the power supply voltage VC be equal to or below a predetermined current value and a voltage value, respectively, so as to make heat generated by the position detecting section 33 be extremely small.

As described above, if the heat generation determining section 44 determines that the voice coil motor 32 is in a heat generating state, the fault processing section 46 halts actuation of the voice coil motor 32 and also halts actuation of the position detecting section 33.

Note that if it is determined that only the voice coil motor 32 is in a heat generating state, it is possible that only actuation of the voice coil motor 32 is halted and actuation of the position detecting section 33 is not halted.

(2) Case where Only the Position Detecting Section Generates Heat

If it is determined that the voice coil motor 32 is not in a heat generating state and the position detecting section 33 is in a heat generating state based on the determination result information pieces J1 and J2, the fault processing section 46 outputs a halt signal SS1 for halting actuation of the voice coil motor driver 41 to the voice coil motor driver 41 and outputs a halt signal S S2 for halting actuation of the position detecting section 33 to the position detecting circuit 43.

In other words, if the heat generation determining section 45 determines that the position detecting section 33 is in a heat generating state, the fault processing section 46, which serves as an actuation halting section, halts actuation of the position detecting section 33. More specifically, the fault processing section 46 makes the power supply voltage VC for the differential amplifier 38 be zero or no more than a predetermined voltage value and makes the input current IC for the Hall element 37 be zero or no more than a predetermined current value.

Furthermore, if the heat generation determining section 45 determines that the position detecting section 33 is in a heat generating state, the fault processing section 46 halts actuation of the position detecting section 33 and also halts actuation of the voice coil motor 32. The halt of the actuation of the voice coil motor 32 is performed by the drive control section 42 configured to control driving of the voice coil motor 32. This is because if actuation of the position detecting section 33 is halted, feedback control of the voice coil motor 32 fails to be normally performed.

As a result, supply of the current and the voltage to the position detecting section 33 is prevented and supply of the drive current DI to the voice coil motor 32 is also prevented.

Note that in this case, since the voice coil motor 32 is normal, it is possible that the zoom lens 35*a* is driven with an output of the drive current DI for the voice coil motor 32 set to a predetermined value to bring a zoom position to a wide angle position so that a surgeon can easily pull the endoscope out from the inside of a body while viewing an endoscopic image. As indicated by the alternate long and short dash line in FIG. 2, the fault processing section 46 outputs a control signal to the drive control section 42 to cause the voice coil motor driver 41 to output a drive current DI for moving the zoom lens 35*a* so as to bring a zoom position to a wide angle position by means of feedforward control.

In other words, if the heat generation determining section 45 determines that the position detecting section 33 is in a heat generating state and the heat generation determining section 44 does not determine that the voice coil motor 32 is in a heat generating state, the fault processing section 46 drives the voice coil motor 32 to move the position of the lens in the zoom mechanism to the side on which a wider view angle can be secured for an endoscopic image.

(3) Case where Both the Voice Coil Motor and the Position Detecting Section Generate Heat If it is determined that both the voice coil motor 32 and the position detecting section 33 are in a heat generating state based on the determination result information pieces J1 and J2, the fault processing section 46 outputs a halt signal SS1 for halting actuation of the voice coil motor driver 41 to the voice coil motor driver 41 and outputs a halt signal S S2 for halting actuation of the position detecting section 33 to the position detecting circuit 43.

As a result, the supply of the current and the voltage to the position detecting section 33 is prevented and supply of the drive current DI to the voice coil motor 32 is also prevented.

As described above, the above embodiment enables provision of an endoscope apparatus enabling suppression of, e.g., deterioration in characteristics of a position detecting section due to generation of heat by the position detecting section.

Next, modifications of the above-described embodiment will be described.

(Modification 1)

In the above-described embodiment, whether or not the actuator is in a heat generating state is determined based on a magnitude of a value of a current supplied to the actuator, that is, the voice coil motor 32, but may be determined based on a magnitude of a load resistance value of the actuator.

FIG. 7 is a circuit diagram of a voice coil motor driver 41 where whether or not an actuator is in a heat generating state is determined based on a resistance value of the actuator, according to modification 1. The voice coil motor driver 41 according to modification 1 includes a current detecting section 52.

The current detecting section 52 is provided on a path of a drive current DI flowing in a voice coil motor 32. A voltage value signal AV of a power supply voltage VCC for the voice coil motor 32 from a drive control section 42 and a current value signal dI of a drive current DI from the current detecting section 52 are inputted to a heat generation determining section 44 for the actuator.

The heat generation determining section 44 determines whether or not the voice coil motor 32 is in a heat generating state based on a resistance value r calculated from the voltage value signal AV of the voltage applied from the drive control section 42 to the voice coil motor 32 and the current value signal dI detected by the current detecting section 52.

For example, when a part of the drive current DI leaks because of a short with an outer covering member inside the distal end portion 21, a current value indicated by the current value signal dI decreases, but in reality, a current flowing in the voice coil motor 32 may be large and the voice coil motor 32 may be in a heat generating state. Also, if the voice coil motor 32 fails to move because of a fault, the drive current DI increases under feedback control. If such situation occurs, the voice coil motor 32 may enter a heat generating state.

The heat generation determining section 44 determines such situation based on the resistance value r and the current value signal dI. For example, if a state in which the resistance value r is a predetermined threshold rth1 or greater or the current value signal dI is a predetermined threshold dIth1 or greater continues for a predetermined time period T3 or more, the heat generation determining section 44 determines that the voice coil motor 32 is in a heat generating state. In other words, if the resistance value r calculated from the current value signal dI detected by the current detecting section 52 provided inside the path of the drive current DI for the voice coil motor 32 and the applied voltage applied to the voice coil motor 32 is the predetermined threshold rth1 or greater or the current value signal dI is the predetermined threshold dIth1 or greater and a state in which the resistance value r is the predetermined threshold rth1 or greater or the current value signal dI is the predetermined threshold dIth1 or greater continues for the predetermined time period T3, the heat generation determining section 44 determines that the voice coil motor 32 is in a heat generating state.

Therefore, modification 1 also enables determination of whether or not an actuator generates heat.

(Modification 2)

In the above embodiment, whether or not the actuator is in a heat generating state is determined based on a magnitude of a value of a current supplied to the actuator, that is, the voice coil motor 32, but it is possible that if a state in which a difference between a control target value and a detected value is a predetermined threshold or greater continues for a predetermined time period or more in the drive control section 42, the voice coil motor 32 is determined as being in a heat generating state.

As described above, the drive control section 42 performs feedback control of a zoom position based on zoom position information PI from the position detecting circuit 43 and generates a drive instruction signal DS as a control signal and outputs the drive instruction signal DS to the voice coil motor driver 41 so that a zoom lens 35a is moved to a zoom position designated by a zoom instruction signal ZC.

In modification 2, if a difference between a lens position of a zoom lens 35a indicated by zoom position information PI and a control target value designated by a zoom instruction signal ZC is a predetermined threshold THD or greater and a state in which the difference from the control target value is the predetermined threshold THD or greater continues for a predetermined time period T4 or more, a heat generation determining section 44 presumes or determines that a voice coil motor 32 is at fault and is in a heat generating state.

In FIG. 2, as indicated by the alternate long and two short dashes line, the drive control section 42 supplies the zoom position information PI and the control target value information of the zoom instruction signal ZC to the heat generation determining section 44.

If a state in which the difference between the control target value and the detected value is the predetermined threshold THD or greater continues for the predetermined time period T4 or more, the heat generation determining section 44 determines that the voice coil motor 32 is in a heat generating state.

Therefore, modification 2 enables determination of whether or not an actuator generates heat.

(Modification 3)

In the above-described embodiment, the heat generation determining sections 44 and 45 determines whether or not the actuator generates heat and whether or not the position detecting section generates heat based on the current supplied to the voice coil motor 32, and the current supplied to the position detecting section 33 and the power supply voltage, respectively, but whether or not the actuator generates heat and whether or not the position detecting section generates heat may be determined by respective temperature sensors.

In FIG. 2, as indicated by a dotted line, a temperature sensor 71 is arranged in the vicinity of a voice coil motor 32.

A heat generation determining section 44 calculates a temperature of the voice coil motor 32 based on an output signal from the temperature sensor 71, and if a state in which the calculated temperature is a predetermined threshold TH4 or greater continues for a predetermined time period T5 or more, determines that the voice coil motor 32 is in a heat generating state.

In other words, the heat generation determining section 44 determines that the voice coil motor 32 is in a heat generating state based on an output signal from the temperature sensor 71 provided in the voice coil motor 32.

Furthermore, likewise, as indicated by a dotted line in FIG. 2, a temperature sensor 72 is arranged in the vicinity of a position detecting section 33.

The heat generation determining section 45 calculates a temperature of the position detecting section 33 based on an output signal from the temperature sensor 72, and if a state in which the calculated temperature is a predetermined threshold TH5 or greater continues for a predetermined time period T6 or more, determines that the position detecting section 33 is in a heat generating state.

In other words, the heat generation determining section 45 determines that the position detecting section 33 is in a heat generating state based on an output signal of the temperature sensor 72 provided in the position detecting section 33.

Therefore, modification 3 also enables determination of whether or not an actuator or a position detecting section generates heat.

(Modification 4)

In the above-described embodiment, the two heat generation determining sections 44, 45 and the fault processing section 46 of the control section 40 are provided inside the video processor 3 but may be provided inside the connector 13a.

As described above, the embodiment and respective modifications described above each enable provision of an endoscope apparatus that enables suppression of, e.g., deterioration in characteristics of a position detecting section due to generation of heat by the position detecting section.

The present invention is not limited to the above-described embodiment and various changes, alterations and the like are possible without departing from the spirit of the present invention.

What is claimed is:

1. An endoscope apparatus comprising:
an endoscope including an observation optical system, the observation optical system including a lens drive mechanism; and
an image processing apparatus including a processor including hardware, the image processing apparatus being connected to the endoscope, the endoscope apparatus comprising:
an actuator provided in the endoscope and configured to drive a lens relating to the lens drive mechanism;
a memory configured to store determination information for a heat generation determination; and
a position detecting sensor provided in the endoscope, the position detecting sensor being configured to detect a position of the lens by being supplied with an input voltage and an input current and outputting a position detection signal,
the processor being configured to:
determine whether or not the position detecting sensor is in a first heat generating state based on the determination information and one or more of the input voltage or the input current; and
if the position detecting sensor is determined to be in the first heat generating state, make the input current and the input voltage supplied to the position detecting sensor be zero so as to halt actuation of the position detecting sensor, or make the input current and the input voltage supplied to the position detecting sensor be equal to or below a predetermined current value so as to reduce heat generated by the position detecting sensor.

2. The endoscope apparatus according to claim 1, wherein if it is determined that the position detecting sensor is in the first heat generating state, the processor is configured to halt actuation of the position detecting sensor and halt actuation of the actuator.

3. The endoscope apparatus according to claim 1, wherein the processor is configured to:
monitor the input current or the input voltage inputted to the position detecting sensor, and
if a value of the input current or the input voltage is a first threshold or greater and a state in which the value of the input current or the input voltage is the first threshold or greater continues for a first period of time, determine that the position detecting sensor is in the first heat generating state.

4. The endoscope apparatus according to claim 1, wherein the processor is configured to determine that the position detecting sensor is in the first heat generating state based on an output signal from a temperature sensor provided in the position detecting sensor.

5. The endoscope apparatus according to claim 1, wherein the processor is configured to:
determine whether or not the actuator is in a second heat generating state, and
if the actuator is determined to be in the second heat generating state, halt actuation of the actuator.

6. The endoscope apparatus according to claim 1, wherein the processor is configured to:
determine whether or not the actuator is in a second heat generating state, and
if the actuator is determined to be in the second heat generating state, halt actuation of the actuator and halt actuation of the position detecting sensor.

7. The endoscope apparatus according to claim 5, wherein if the processor determines that the position detecting sensor is in the first heat generating state and determines that the actuator is not in the second heat generating state, the processor is configured to drive the actuator to move the position of the lens in the lens drive mechanism to a position resulting in a wider field of view for an endoscopic image.

8. The endoscope apparatus according to claim 5, wherein the processor is configured to:
monitor a supply current supplied to the actuator; and
if a value of the supply current is a first threshold or greater and a state in which the value of the supply current is the first threshold or greater continues for a first period of time, determine that the actuator is in the second heat generating state.

9. The endoscope apparatus according to claim 8, wherein if a resistance value calculated from the supply current supplied to the actuator and an applied voltage applied to the actuator is a second threshold or greater and a state in which the resistance value is the second threshold or greater continues for a second period of time, the processor is configured to determine that the actuator is in the second heat generating state.

10. The endoscope apparatus according to claim 5, wherein the processor is further configured to:
drive the actuator using feedback control based on the detected position of the lens, and
if a difference between the detected position of the lens and a control instruction value for the position of the lens is a first threshold or greater and a state in which the difference is the first threshold or greater continues for a first period of time, determine that the actuator is in the second heat generating state.

11. The endoscope apparatus according to claim 5, wherein the processor is configured to determine that the actuator is in the second heat generating state based on an output signal from a temperature sensor provided in the actuator.

12. The endoscope apparatus according to claim 1, wherein the actuator is a voice coil motor including one or more magnets and one or more coils and enabling a movable portion to be moved relative to a fixed portion.

13. The endoscope apparatus according to claim 1, wherein:
the position detecting sensor includes a Hall element or a magnetic resistance element configured to detect a change of a magnetic field resulting from movement of the lens; and
the Hall element or the magnetic resistance element receives supply of a constant current from a constant current circuit.

14. An endoscope apparatus comprising:
an endoscope including an observation optical system, the observation optical system including a lens drive mechanism; and
an image processing apparatus including a processor including hardware, the image processing apparatus being connected to the endoscope, the endoscope apparatus comprising:
an actuator provided in the endoscope and configured to drive a lens relating to the lens drive mechanism; and
a position detecting sensor provided in the endoscope, the position detecting sensor being configured to detect a position of the lens,
the processor being configured to:
monitor an input current or an input voltage inputted to the position detecting sensor;
if a value of the input current or the input voltage is a first threshold or greater and a state in which the value of the input current or the input voltage is the first threshold or greater continues for a first period of time, determine that the position detecting sensor is in a first heat generating state; and
if the processor determines that the position detecting sensor is determined to be in the first heat generating state, halt actuation of the position detecting sensor.

* * * * *